US011204677B2

(12) United States Patent
Palushi et al.

(10) Patent No.: US 11,204,677 B2
(45) Date of Patent: Dec. 21, 2021

(54) METHOD FOR REAL TIME UPDATE OF FLY-THROUGH CAMERA PLACEMENT

(71) Applicants: Acclarent, Inc., Irvine, CA (US); Biosense Webster (Israel) Ltd., Yokneam (IL)

(72) Inventors: Jetmir Palushi, Irvine, CA (US); Henry F. Salazar, Pico Rivera, CA (US); Jordan R. Trott, Redondo Beach, CA (US); Moran Levi, Kiryat-Tivon (IL); Itamar Bustan, Zichron Ya'acov (IL); Yoav Pinsky, Yokneam (IL); Noam Racheli, Hadera (IL); Athanasios Papadakis, Newport Beach, CA (US)

(73) Assignees: Acclarent, Inc., Irvine, CA (US); Biosense Webster (Israel) Ltd., Yokneam (IL)

(*) Notice: Subject to any disclaimer, the term of this patent is extended or adjusted under 35 U.S.C. 154(b) by 0 days.

(21) Appl. No.: 16/577,019

(22) Filed: Sep. 20, 2019

(65) Prior Publication Data
US 2020/0125236 A1 Apr. 23, 2020

Related U.S. Application Data

(60) Provisional application No. 62/748,571, filed on Oct. 22, 2018.

(51) Int. Cl.
*G06F 3/0481* (2013.01)
*G06F 3/0346* (2013.01)
(Continued)

(52) U.S. Cl.
CPC .......... *G06F 3/04815* (2013.01); *A61B 34/20* (2016.02); *A61B 34/25* (2016.02);
(Continued)

(58) Field of Classification Search
CPC ... A61B 2034/107; A61B 34/20; A61B 34/25; A61B 2090/378; A61B 2034/105;
(Continued)

(56) References Cited

U.S. PATENT DOCUMENTS 6,167,296 A * 12/2000 Shahidi ................... A61B 5/06
600/117
7,720,521 B2 5/2010 Chang et al.
(Continued)

FOREIGN PATENT DOCUMENTS

EP 3395282 A1 10/2018

OTHER PUBLICATIONS

International Search Report and Written Opinion dated Jan. 20, 2020 for International Application No. PCT/IB2019/058938, 16 pages.

*Primary Examiner* — Jennifer N Welch
*Assistant Examiner* — K C Chen
(74) *Attorney, Agent, or Firm* — Frost Brown Todd LLC

(57) ABSTRACT

A virtual endoscopic view shows a surgical area and surrounding anatomy and may also show a position of a surgical instrument in use during a surgical procedure, allowing a surgeon to virtually view the surgical area when direct viewing or actual endoscopic views are incomplete, obstructed, or otherwise unavailable or undesirable. In order to render the endoscopic view, an IGS navigation system may be configured with an observer point and an observer orientation within 3-D space based upon user inputs. A user interface for defining these points allows a user to view a virtual endoscopic preview in real-time while providing inputs, thus improving the likelihood that the resulting virtual endoscopic view is as desired by the user; and reducing time spent redefining and reconfiguring the virtual endoscopic view. The virtual endoscopic preview may pro-
(Continued)

vide combinations of static and dynamic images to illustrate the spatial relationship of the provided inputs.

20 Claims, 13 Drawing Sheets

(51) Int. Cl.
*G06F 3/0338* (2013.01)
*G06F 3/01* (2006.01)
*G06T 7/50* (2017.01)
*G06T 15/20* (2011.01)
*G06F 3/0484* (2013.01)
*G16H 30/20* (2018.01)
*G16H 20/40* (2018.01)
*A61B 34/20* (2016.01)
*A61B 34/00* (2016.01)
*A61B 90/00* (2016.01)
*A61B 34/10* (2016.01)

(52) U.S. Cl.
CPC ........ *G06F 3/04842* (2013.01); *G06T 15/205* (2013.01); *G16H 20/40* (2018.01); *G16H 30/20* (2018.01); *A61B 2034/105* (2016.02); *A61B 2090/374* (2016.02); *A61B 2090/378* (2016.02); *A61B 2090/3762* (2016.02); *G06F 2203/04803* (2013.01); *G06T 2200/24* (2013.01); *G06T 2210/41* (2013.01)

(58) Field of Classification Search
CPC ...... A61B 2090/374; A61B 2090/3762; A61B 17/24; A61B 2034/2072; A61B 2034/2051; A61B 2090/365; A61B 90/37; G06F 3/04815; G06F 3/04842; G06F 2203/04803; G06F 3/04812; G06T 15/205; G06T 2200/24; G06T 2210/41; G16H 30/20; G16H 20/40; G16H 30/40; G16H 50/50
See application file for complete search history.

(56) References Cited

U.S. PATENT DOCUMENTS

| | | |
|---|---|---|
| 10,561,370 B2 | 2/2020 | Salazar et al. |
| 2005/0283075 A1* | 12/2005 | Ma .................. G06T 15/08 600/441 |
| 2007/0018975 A1 | 1/2007 | Chuanggui et al. |
| 2007/0238981 A1* | 10/2007 | Zhu .................. A61B 90/36 600/424 |
| 2008/0071141 A1 | 3/2008 | Gattani et al. |
| 2010/0160733 A1 | 6/2010 | Gilboa |
| 2011/0282151 A1* | 11/2011 | Trovato .............. G06T 7/248 600/117 |
| 2013/0250081 A1* | 9/2013 | Pandey ............ A61B 1/00183 348/77 |
| 2014/0364725 A1 | 12/2014 | Makower |
| 2016/0008083 A1 | 1/2016 | Kesten et al. |
| 2018/0178124 A1* | 6/2018 | Noda .................. G06F 3/0481 |
| 2018/0246631 A1* | 8/2018 | Maruyama ............ G06T 19/20 |
| 2018/0280100 A1* | 10/2018 | Reinstein ........... A61B 1/00039 |
| 2020/0077924 A1* | 3/2020 | Hladio ................ A61B 5/1121 |

* cited by examiner

METHOD FOR REAL TIME UPDATE OF FLY-THROUGH CAMERA PLACEMENT

PRIORITY

This application claims priority to U.S. Provisional Patent 62/748,571, filed Oct. 22, 2018 and entitled Method for Real Time Update of Fly-Through Camera Placement, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In order to provide the virtual endoscopic view described above, the IGS navigation system may require "placement" of a virtual "camera" to define the viewpoint presented by the virtual endoscopic view. Such placement may require configurations or inputs defining an observer point (i.e., a point along an x, y, and z-axis in 3-D space at which a viewer of the virtual endoscopic view is located) and an observer orientation (i.e., Euler angles defining a direction in 3-D space that the viewer is facing). Defining locations and orientations in virtual 3-D space can be difficult when using conventional 2D interfaces and tools instead of 3-D capable interfaces and tools.

As an example illustrating the potential difficulty, when using 3-D interfaces and tools, such as a virtual reality head mounted display that is capable of room-scale movement and viewing of a 3-D virtual environment with six degrees of freedom, placement of the virtual camera can be as simple as walking around or using a controller to move within the virtual 3-D space (i.e., moving along the x, y, and z axis) and then looking in the desired direction (i.e., rotating yaw, pitch, and roll).

When using 2D interfaces, such as a computer display and a mouse, navigating and viewing the same 3-D virtual environment in order to define an observer point and orientation may be less intuitive and more error prone. Conventional 2D interfaces may require a user to browse through a number of individual images of the digital map using a keyboard and mouse, and then manually select a point on a first image as either the observer location or orientation, and then select a point on a second image as the remaining point. The first image and the second image might not fall on the same point in the Z-axis (i.e., the third dimension), making it difficult to judge their relation to each other as a 2D observer. As a result, the process of configuring virtual endoscopic views during IGS navigation can be inaccurate (e.g., a user may select the first and second point and then decide after the virtual endoscopic view is rendered that it is not what was desired) and inefficient (e.g., a user may need to re-define the first and second point a number of times in order to achieve the desired perspective).

Such inaccuracy and inefficiency can have a negative impact on outcomes of a surgical procedure, including reducing the quality or availability of viewpoints available through the endoscopic view, and increasing the overall time required to complete the procedure. Thus, it may be advantageous to provide an IGS navigation system with improved features for defining viewpoints and perspectives within a virtual endoscopic view.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
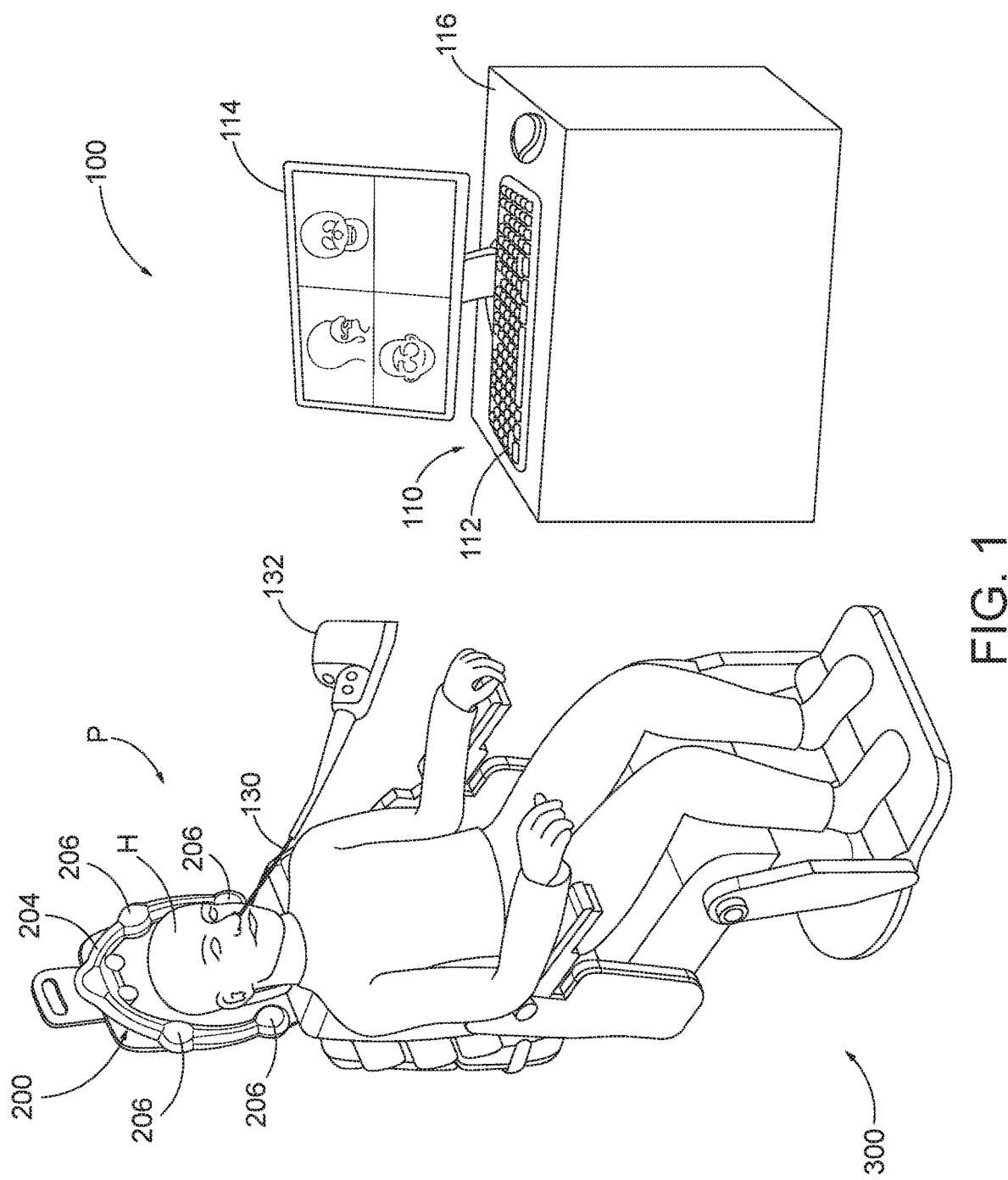
FIG. 1 depicts a schematic view of an exemplary surgery navigation system being used on a patient seated in an exemplary medical procedure chair.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. Exemplary Image Guided Surgery Navigation System

FIG. 1 shows an exemplary IGS navigation system (100) enabling an ENT procedure to be performed using image guidance. In addition to or in lieu of having the components and operability described herein IGS navigation system (100) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (100) of the present example comprises a field generator assembly (200), which comprises set of magnetic field generators (206) that are integrated into a horseshoe-shaped frame (204). Field generators (206) are operable to generate alternating magnetic fields of different frequencies around the head (H) of the patient (P). Navigation guidewire (130) may be a standalone device or may be positioned on an end effector or other location of a medical instrument such as a surgical cutting instrument or dilation instrument. In the present example, frame (204) is mounted to a chair (300), with the patient (P) being seated in the chair (300) such that frame (204) is located adjacent to the head (H) of the patient (P). By way of example only, chair (300) and/or field generator assembly (200) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561, 370 on Feb. 18, 2020, the disclosure of which is incorporated by reference herein.

IGS navigation system (100) of the present example further comprises a processor (110), which controls field generators (206) and other elements of IGS navigation system (100). For instance, processor (110) is operable to drive field generators (206) to generate alternating electromagnetic fields; and process signals from navigation guidewire (130) to determine the location of a sensor in navigation guidewire (130) within the head (H) of the patient (P). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Navigation guidewire (130) includes a sensor (not shown) that is responsive to positioning within the alternating magnetic fields generated by field generators (206). A coupling unit (132) is secured to the proximal end of navigation guidewire (130) and is configured to provide communication of data and other signals between console (116) and navigation guidewire (130). In the present example, the sensor of navigation guidewire (130) comprises at least one coil at the distal end of navigation guidewire (130). When such a coil is positioned within an alternating electromagnetic field generated by field generators (206), the alternating magnetic field may generate electrical current in the coil, and this electrical current may be communicated along the electrical conduit(s) in navigation guidewire (130) and further to processor (110) via coupling unit (132). This phenomenon may enable IGS navigation system (100) to determine the location of the distal end of navigation guidewire (130) or other medical instrument (e.g., dilation instrument, surgical cutting instrument, etc.) within a three-dimensional space (i.e., within the head (H) of the patient (P), etc.). To accomplish this, processor (110) executes an algorithm to calculate location coordinates of the distal end of navigation guidewire (130) from the position related signals of the coil(s) in navigation guidewire (130).

Processor (110) uses software stored in a memory of processor (110) to calibrate and operate IGS navigation system (100). Such operation includes driving field generators (206), processing data from navigation guidewire (130), processing data from operating controls (112), and driving display screen (114). In some implementations, operation may also include monitoring and enforcement of one or more safety features or functions of IGS navigation system (100). Processor (110) is further operable to provide video in real time via display screen (114), showing the position of the distal end of navigation guidewire (130) in relation to a video camera image of the patient's head (H), a CT scan image of the patient's head (H), and/or a computer generated three-dimensional model of the anatomy within and adjacent to the patient's nasal cavity. Display screen (114) may display such images simultaneously and/or superimposed on each other during the surgical procedure. Such displayed images may also include graphical representations of instruments that are inserted in the patient's head (H), such as navigation guidewire (130), such that the operator may view the virtual rendering of the instrument at its actual location in real time. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head (H).

II. Exemplary Interface and Method for Real-Time Camera Placement

Figure 2:
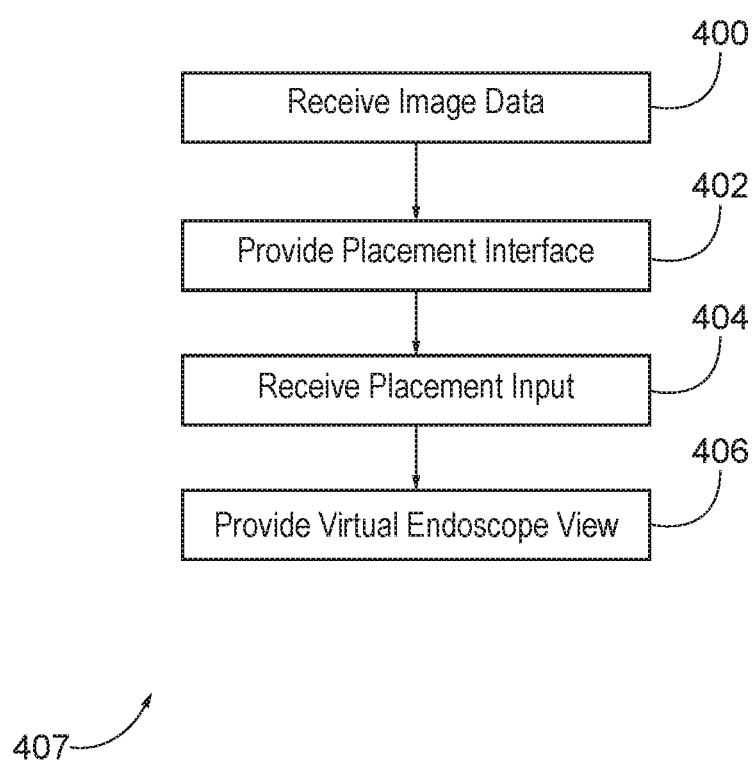
FIG. 2 shows an exemplary set of high level steps that may be performed by or with the surgery navigation system of FIG. 1 to place a virtual camera.

It may be advantageous to provide improved interfaces and methods that allow users additional control and visual context when placing a virtual camera. A clinician or other user using such interfaces and methods may be able to place and modify the view of a virtual camera more quickly and accurately prior to and during a surgical procedure, which may reduce the need for replacement or adjustment, reduce overall procedure time, improve patient outcomes, and provide other benefits. As an example of such a method, FIG. 2 shows an exemplary set of high level steps (407) that may be performed by or with a surgery navigation system such as the IGS navigation system (100) to place a virtual camera.

The IGS navigation system (100) may receive (block 400) preoperative image data from one or more sources such as a hospital information system or procedure information system where such image data may be stored after it is captured. As has been described, the preoperative image data may be used with the IGS navigation system (100) to provide IGS features during a surgical procedure, including a virtual camera positioned to provide a virtual camera view via a device such as the display (114). The IGS navigation system (100) may provide (block 402) a placement interface via the display (114) that a clinician may use to provide inputs defining the virtual camera position and orientation via an input device such as the operating controls (112). As placement inputs are received (block 404) from the clinician, the IGS navigation system (100) will update the placement interface in real-time to provide (block 406) a virtual endoscopic view or preview that may be used by the clinician to preview and provide additional placement inputs prior to a procedure, to modify placement during performance of a surgical procedure, or both.

Figure 3:
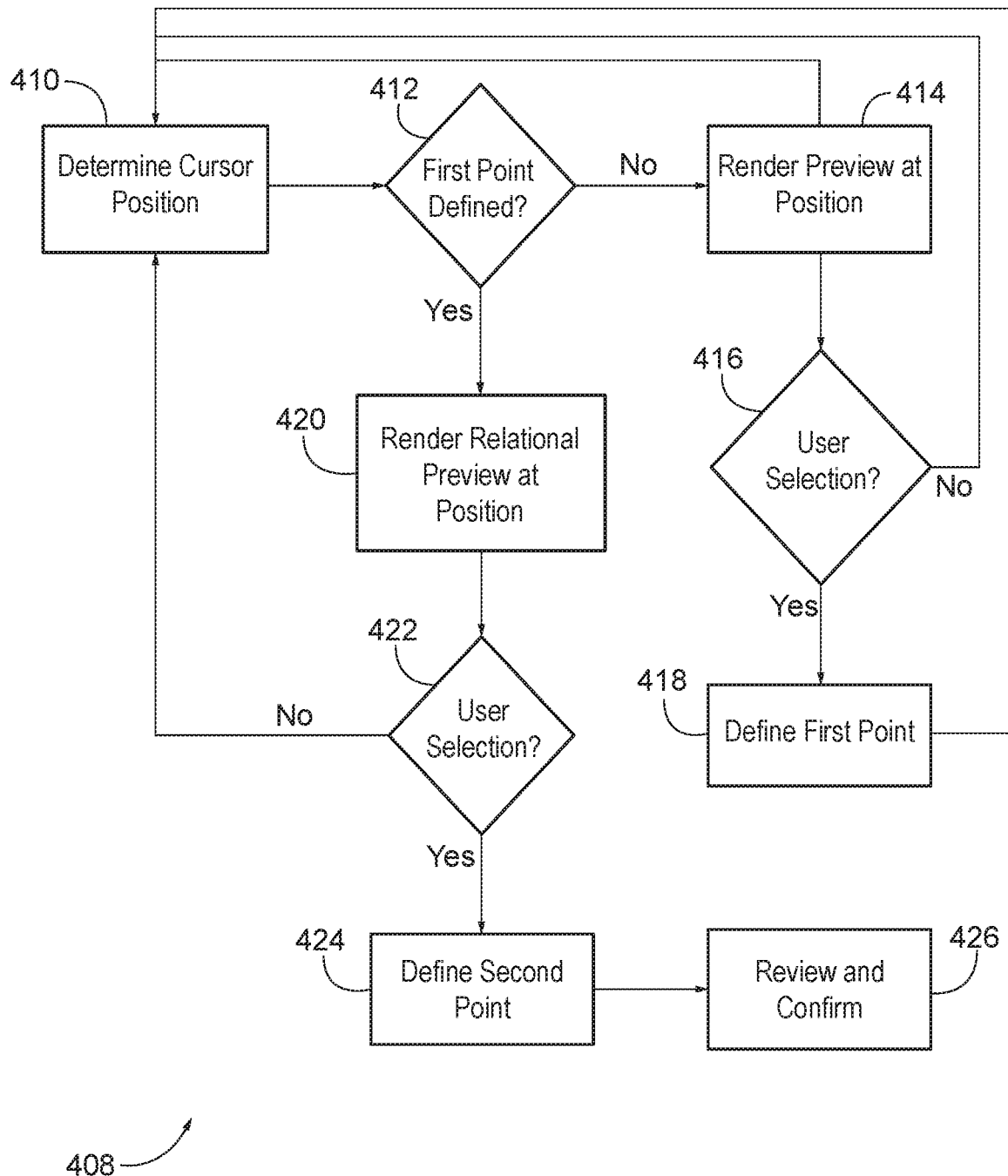
FIG. 3 shows an exemplary set of steps that may be performed by or with the surgery navigation system to provide a real-time virtual endoscopic preview during placement of a virtual camera.

FIG. 3 shows an exemplary set of steps (408) that may be performed by or with a surgery navigation system such as the IGS navigation system (100) to provide (block 406) a real-time virtual endoscopic preview during placement (block 404) of a virtual camera. This real-time virtual endoscopic preview may be provided via a placement interface, such as that shown FIGS. 5-9. Those figures show simulated screenshots of an exemplary placement interface (500) that may be provided by a system performing steps such as those shown in FIGS. 2-4. The placement interface (500) of FIG. 5 shows a set of navigation controls (502) operable to navigate through preoperative image sets and adjust a virtual camera view (516), several preoperative image panes including a frontal image (504), a frontal render (514), a side image (510), and a top-down image (512). The placement interface (500) also comprises a perspective indicator (506) for each preoperative image pane showing the perspective from which the preoperative image is being viewed, and a cursor (508) that a user may interact with via the operating controls (112) to make selections or other interactions with the placement interface (500). Varying implementations may have different numbers of preoperative image panes within the set of preoperative image panes (e.g., the set of preoperative image panes may comprise one or more preoperative image panes).

Placement of the virtual camera in the steps of FIG. 3 is achieved by receiving a set of two inputs from a user that may be used to define a first point and a second point within the set of preoperative images. Since the set of preoperative images can be used by the IGS navigation system (100) to render a 3-D virtual space, the first point and the second point can also be interpreted as existing as discrete points in 3-D space. In this manner, the first point and the second point can be used to define a virtual camera location (e.g., where one point may be used to define a point along an x, y, and z-axis in the 3-D space at which a viewer of the virtual camera view is located) and a virtual camera orientation (e.g., where the other point may be used to define a point in 3-D space that a virtual camera positioned at the first point is facing). It should be understood that, depending upon a particular implementation, the first point may be the virtual camera's location (e.g., a point at which an observer is viewing from) or the virtual camera's orientation (e.g., a point that the observer is viewing). In implementations where the first point is the virtual camera's orientation, the second point may be the virtual camera's location, and vice-versa. Some implementations may support multiple selection models, such as where a user may choose to select the points in a desired order.

Returning to FIG. 3, in order to provide the above functionality, as a user interacts with the placement interface (500), the IGS navigation system (100) may determine (block 410) a position of the cursor (508) and, if a first point has not been defined (block 412), may render (block 414) a real-time virtual endoscopic preview in the virtual camera view (516) based upon the position of the cursor over one of the preoperative images. The real-time virtual endoscopic preview may include depictions of 3-D models of patient anatomy (e.g., which may be built and rendered from pre-operative imaging), may include image slices and other types of preoperative imaging (e.g., CT image slices, MRI image slices, ultrasound image slices), or both. In FIG. 5, it can be seen that the virtual camera view (516) is blank. The virtual camera view may be blank or may show arbitrary image data where the first point has not been defined (block 412), and where the cursor (508) is not positioned within one of the preoperative image panes. As can be seen in FIG. 5, the cursor (508) is positioned at an arbitrary location between the preoperative image panes and the set of navigation controls (502). As a result, when the IGS navigation system (100) attempts to render (block 414) a preview based upon the cursor (508) position, there may be no preview image to show, or an arbitrary preview image.

Figure 6:
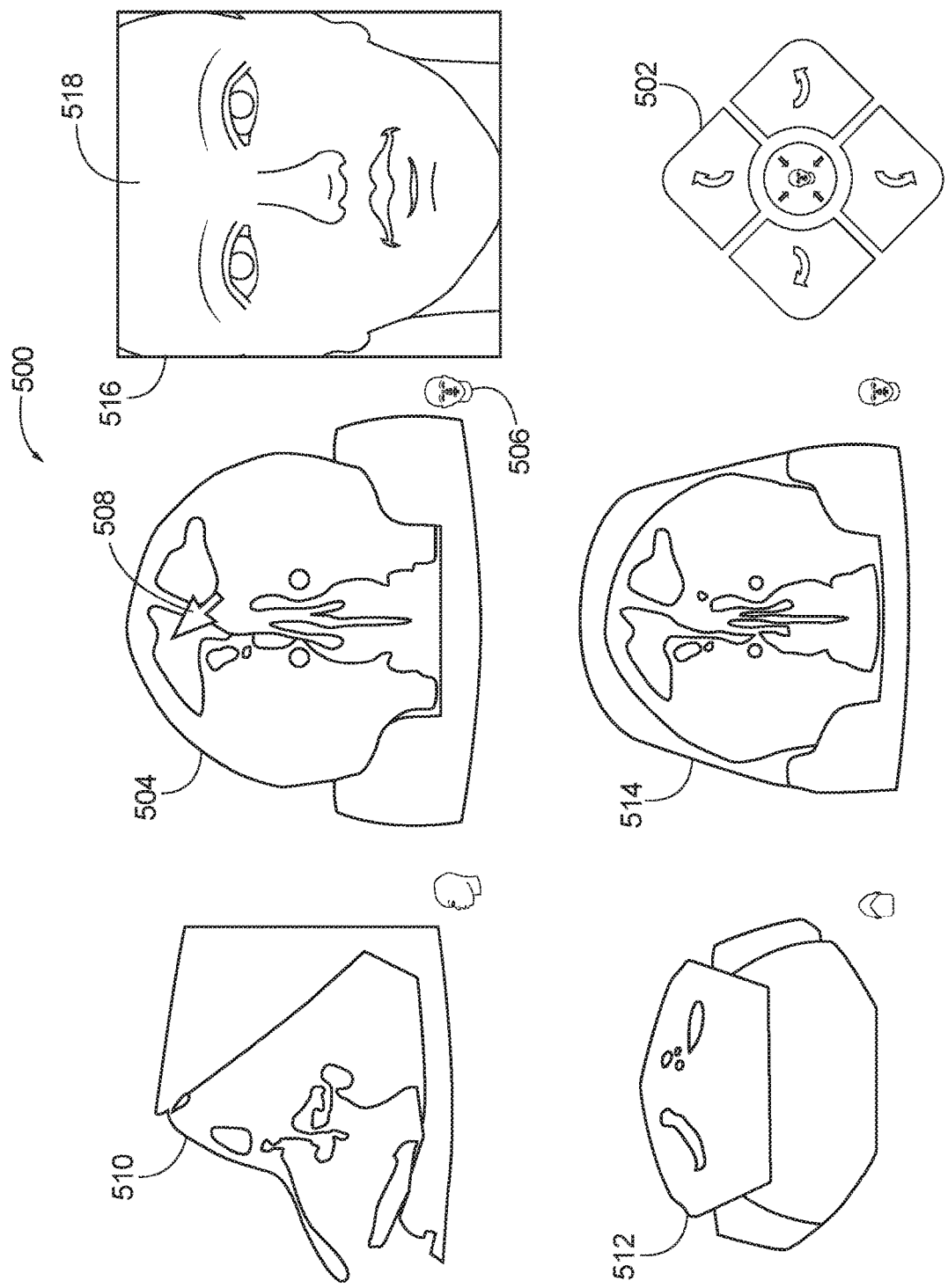
FIG. 6 shows a simulated screenshot of the placement interface of FIG. 5 providing a first preview.

FIG. 6 shows the placement interface (500) during a first preview, prior to defining (block 412) the first point. Here it can be seen that the virtual camera view (516) shows a virtual rendered image of an exterior of a patient's face (518). This is because the cursor (508) is now positioned over the frontal image (504). When the IGS navigation system (100) determines (block 410) that the first point has not been defined (block 412), and that the cursor (508) is now positioned over the frontal image, it may render (block 414) the real-time virtual endoscopic preview based upon the cursor (508) position. Since the cursor (508) is positioned over the frontal image (504), the virtual camera view (516) shows (block 414) a rendered image (518) having the same position and orientation as that of the frontal image (504). Thus, if the cursor (508) were positioned over a location on the side image (510) or the top-down image (512), the virtual camera view (516) would instead show a rendered image of the exterior of a patient's face or head from the side or from above respectively. In this manner, the IGS navigation system (100) is effectively treating the cursor (508) position on a preoperative image pane as the first point in 3-D space; and the perspective of the frontal image (504) (i.e., as indicated by the perspective indicator (506)) as the second point in 3-D space, and then providing the user a preview via the virtual camera view (516) of the perspective a user would have from a virtual camera using that first and second point.

Figure 7:
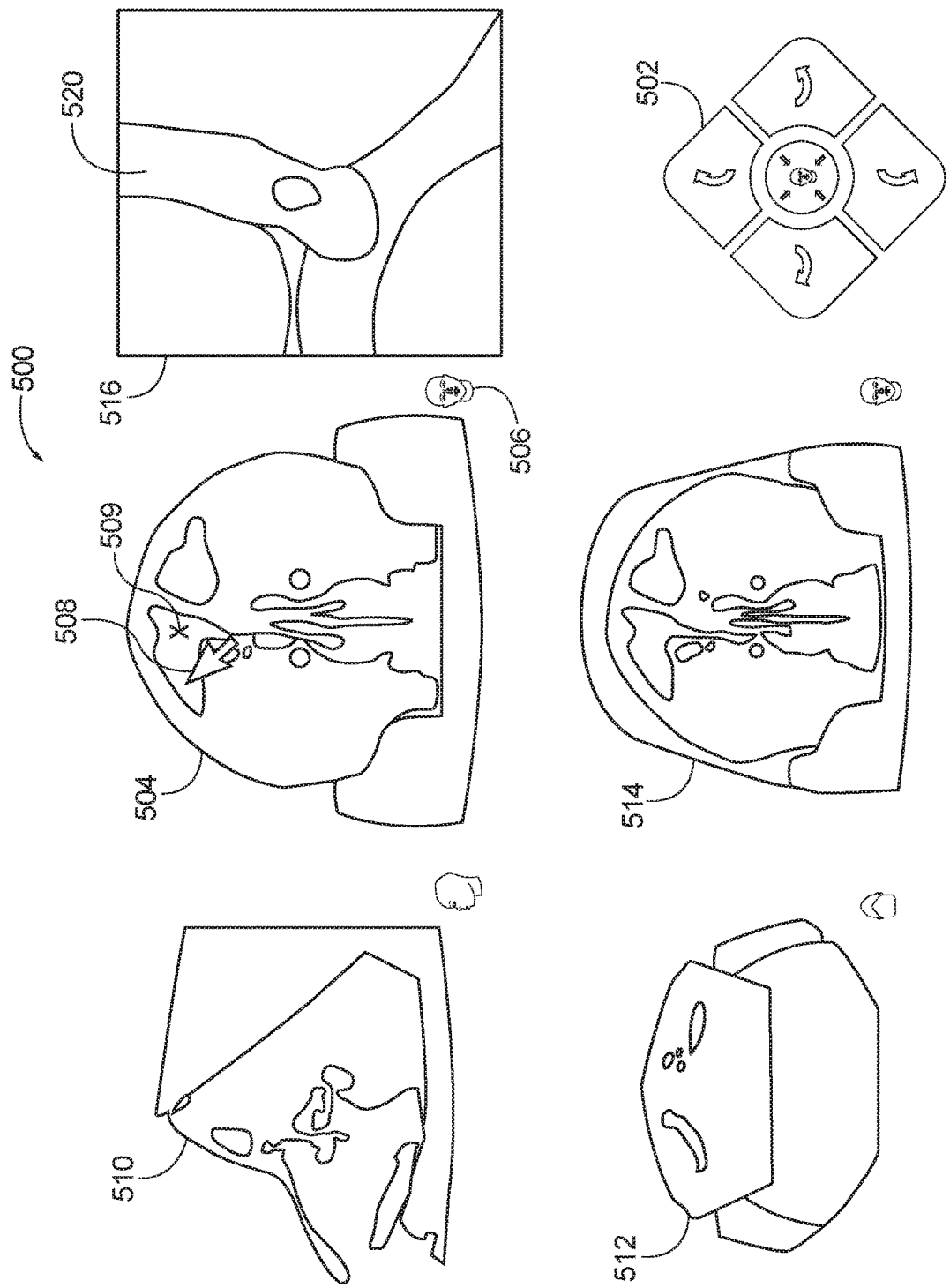
FIG. 7 shows a simulated screenshot of the placement interface of FIG. 5 providing a second preview.

FIG. 7 shows the placement interface (500) during a second preview, after receiving (block 416) a user selection of a location of the cursor (508). When a user selects (block 416) (e.g., by clicking a mouse, keyboard, or other input device associated with the cursor (508)) a location using the cursor (508), that location may be defined (block 418) as the first point (e.g., either the virtual camera's orientation or position). When the first point is defined (block 412), the IGS navigation system (100) may then render (block 420) a relational preview in the virtual camera view (516) based upon the defined (block 418) first point and the determined (block 410) cursor (508) position. Rather than rendering an external view (518) as in FIG. 6, or another view that relies on the perspective of the frontal image (504), the IGS navigation system (100) may instead use the defined (block 418) first point as the first point in 3-D space, and the determined (block 410) cursor position as the second point in 3-D space when providing the real-time virtual endoscopic preview.

As an example of this, in FIG. 7, it can be seen that the cursor (508) has moved from the location of the defined first point (509). The IGS navigation system may determine (block 410) the new cursor position, and since the first point (509) is defined (block 412), may render (block 420) the relational preview based upon the first point (509) and using the determined (block 410) cursor (508) position as the second point. As a result, the virtual camera view (516) shows an interior anatomy view (520) that is viewable from the first point (509) when facing the determined (block 410) cursor (508) position as the second point. As has been discussed, in implementations where the first point (509) is the orientation, the virtual camera view (516) shows the interior anatomy view (520) that is viewable from a virtual camera positioned at the determined (block 410) cursor position, and oriented towards the first point (509). While the described example shows the first point (509) and the second point being on the same plane (i.e., both are selected or determined from the frontal image which depicts a single plane from a fixed perspective), it should be understood that the first and second points could be selected from or determined from the cursor (508) being positioned on any one or more of the preoperative image panes. For example, if the cursor (508) were to be placed over the side image (510) but the first point (509) remained on the frontal image (504), the virtual camera view (516) would preview a different interior anatomy of the patient.

Figure 8:
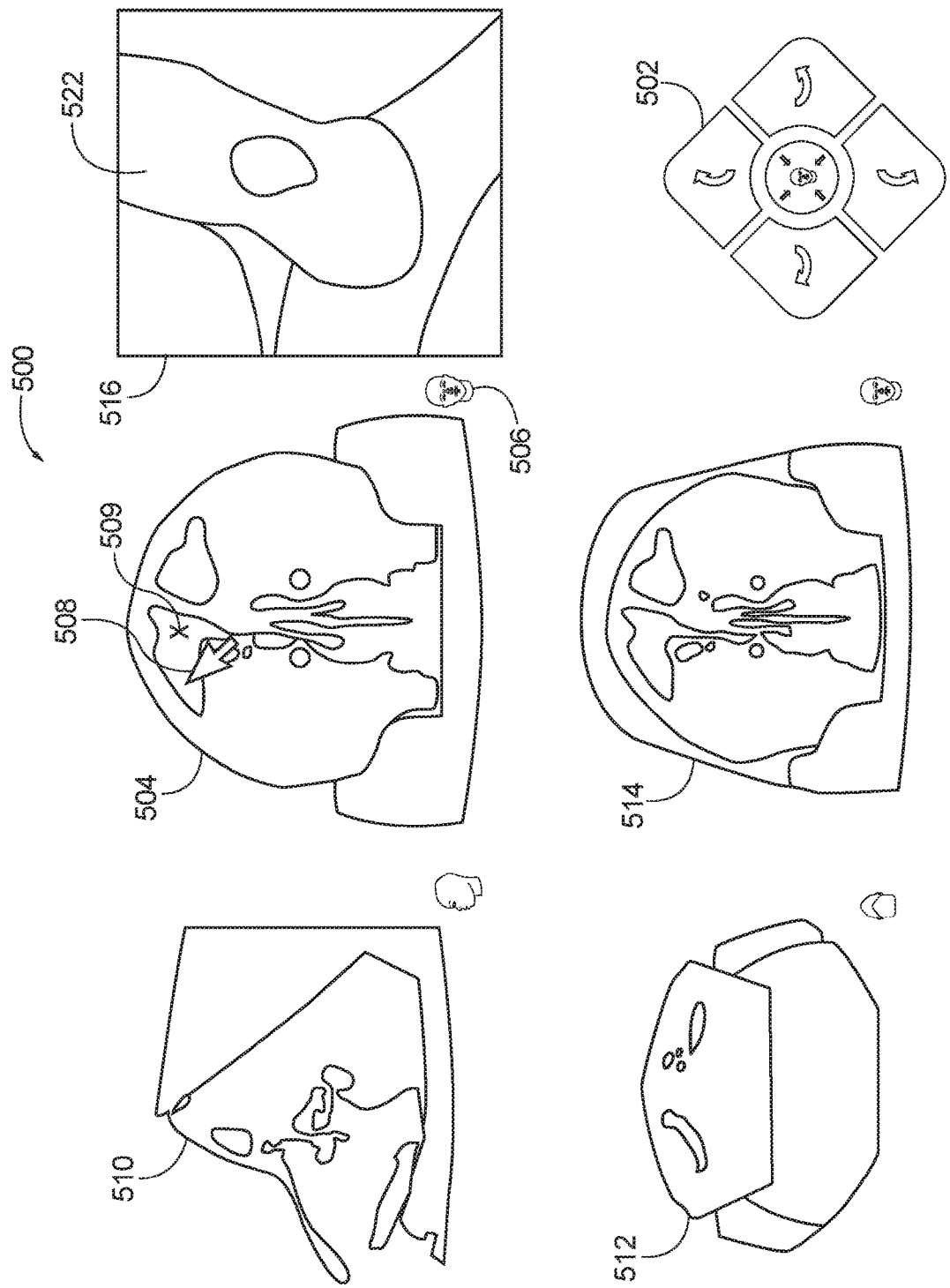
FIG. 8 shows a simulated screenshot of the placement interface of FIG. 5 providing a third preview.
Figure 9:
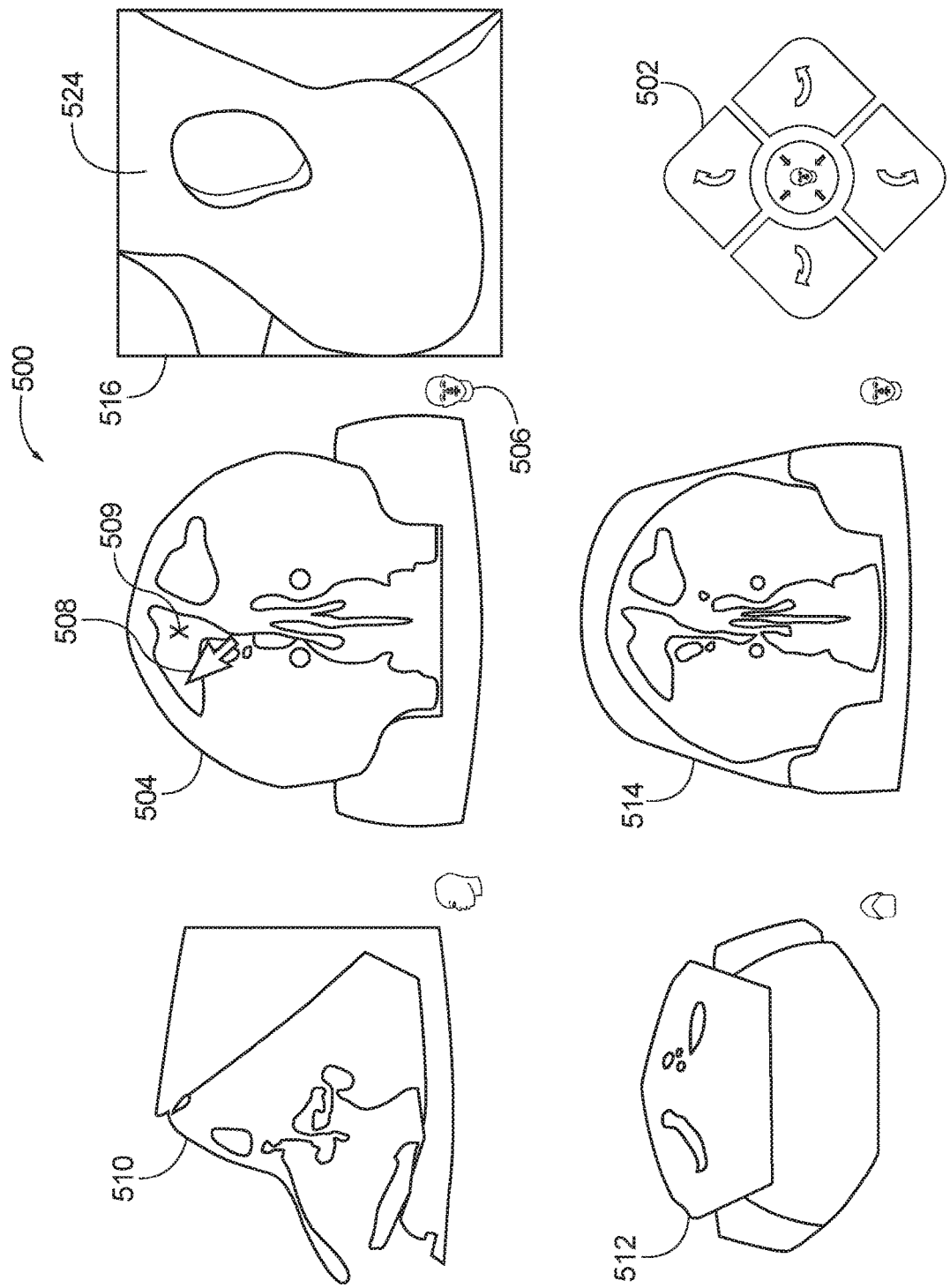
FIG. 9 shows a simulated screenshot of the placement interface of FIG. 5 providing a fourth preview.

As described above, the rendered (block 420) relational preview shows a view that is dependent upon the relationship of the first and second point in 3-D space. This relational preview may also be dynamically rendered, to provide additional visual and spatial context of the relationship between the first and second point. In some implementations, the virtual camera view (516) may travel along or "fly-through" the line or route formed between the first and second point in 3-D space. This effect is simulated in the virtual camera view (516) in FIGS. 7-9, as it can be seen that the virtual camera view (516) sequentially renders the interior anatomy view (520), followed by a first progressive interior anatomy view (522), followed by a second progressive interior anatomy (524), and so on. Such sequential rendering may include every intervening preoperative image, or a subset of intervening preoperative images, and may be rendered at various speeds and framerates as may be desirable. This fly-through effect allows the viewer of the virtual camera view (516) to virtually travel through and view the 3-D space and anatomical structures surrounding the line or route between the first and second points. In FIGS. 7-9 this is perceived as starting at the first point (509), and then gradually moving towards the second point (i.e., the determined (block 410) cursor position in the case of FIG. 7-9), causing the anatomical structures shown in the interior anatomy view (520) to gradually become closer and more visible, and in some cases, even passing through those structures shown in interior anatomy view (520) if the second point is located on the other side.

While the features and the placement interface (500) are described above as displaying a 3-D rendered model of patient anatomy with the virtual camera view (516) (e.g., the interior anatomy view (520)), it should be understood that the same or similar features and interfaces may display other types of images that may be registered with the IGS navigation system (100). This may include, for example, CT image slices, MRI image slices, and ultrasound image slices. An example is shown in FIGS. 10-13, which depict an alternate placement interface (600), which is shown to display images other than 3-D rendered anatomy models. The placement interface (600) in FIG. 10 includes many of the features of the placement interface (500) shown in FIG. 7, such as the set of navigation controls (502), the frontal image (504), the perspective indicators (506), the side image (510), the top-down image (512), the frontal render (514), and the virtual camera view (516), having similar features and function as described in the context of FIG. 7.

Figure 10:
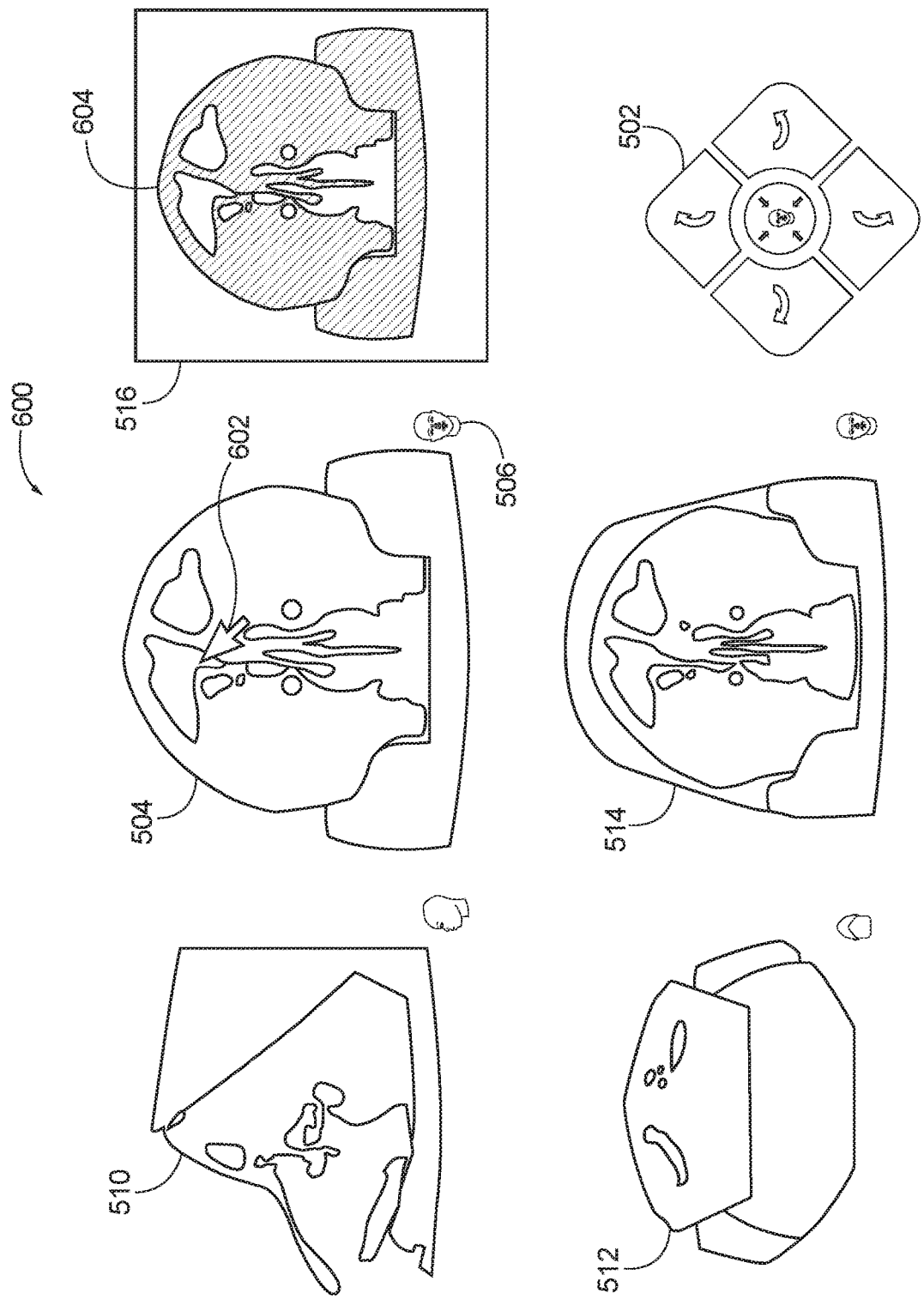
FIG. 10 shows a simulated screenshot of an alternate exemplary placement interface providing a first preview.

As shown in FIG. 10, a cursor (602) is positioned over the frontal image (504), prior to the first point being defined (block 418). The virtual camera view (516) displays an image slice (604) (e.g., a CT image slice, MRI image slice, ultrasound image slice, or other image), which may be selected by a user of the system or may be automatically selected upon other factors (e.g., the position of a tracked instrument, the position of the cursor (602)), for example.

Figure 11:
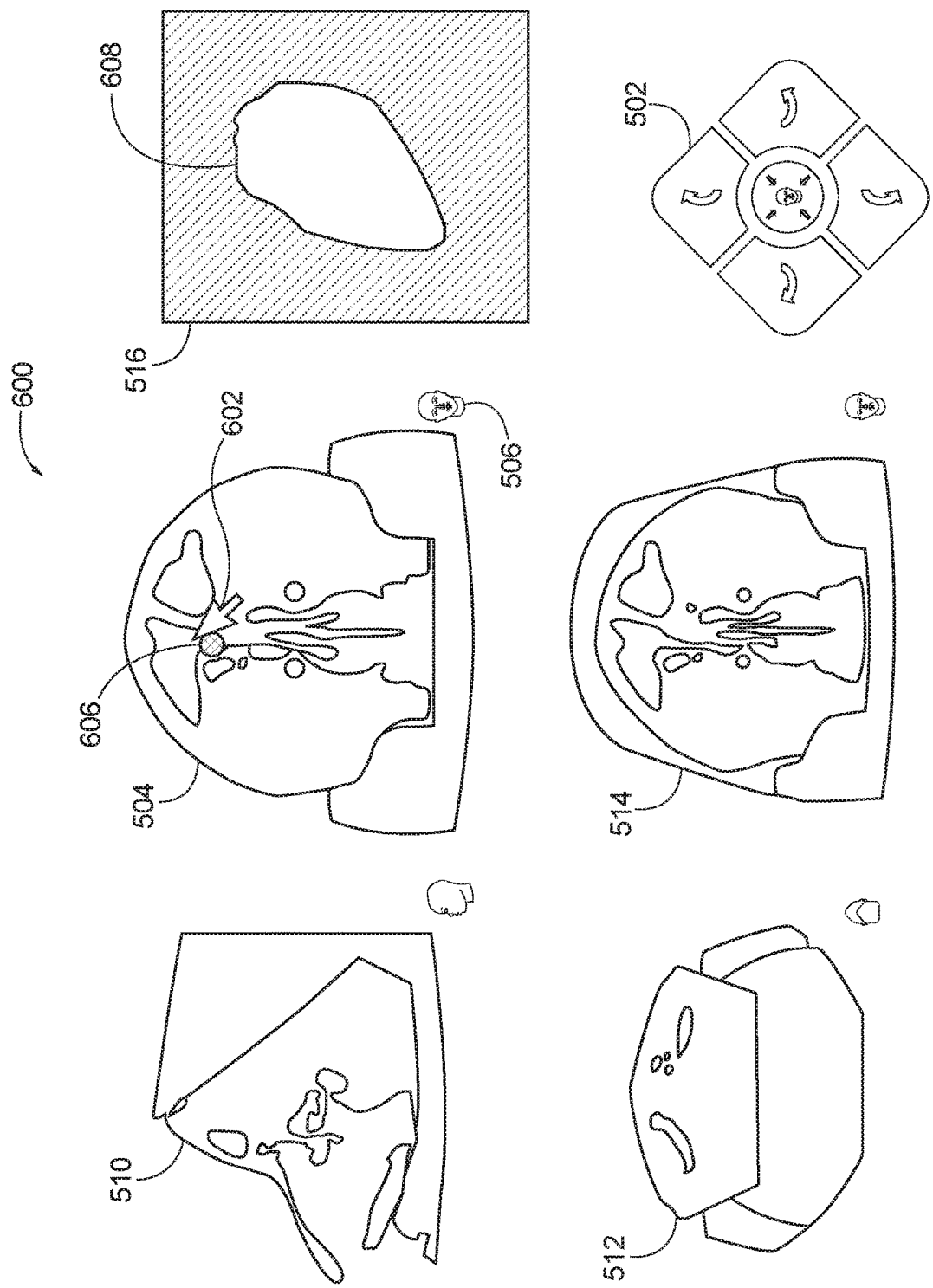
FIG. 11 shows a simulated screenshot of the alternate placement interface of FIG. 10 providing a second preview.

In FIG. 11, the cursor (602) has moved to a new position after the definition (block 418) of the first point, and a marker (606) is rendered on the frontal image (504) indicating the defined (block 418) first point. The virtual camera view (516) now displays a portion (608) of an image slice that has been determined and selected from a plurality of image slices based upon the defined (418) first point and the current position of the cursor (602). In this example, since each of the marker (606) and the cursor (602) are present on a single image slice (e.g., the frontal image (504)), the portion (608) is selected from an image slice that horizontally intersects the frontal image (504), and is depicted at various scaled based upon the distance between the cursor (602) and the bone, tissue, or other characteristics depicted in the image slice that the portion (608) is selected from.

Figure 12:
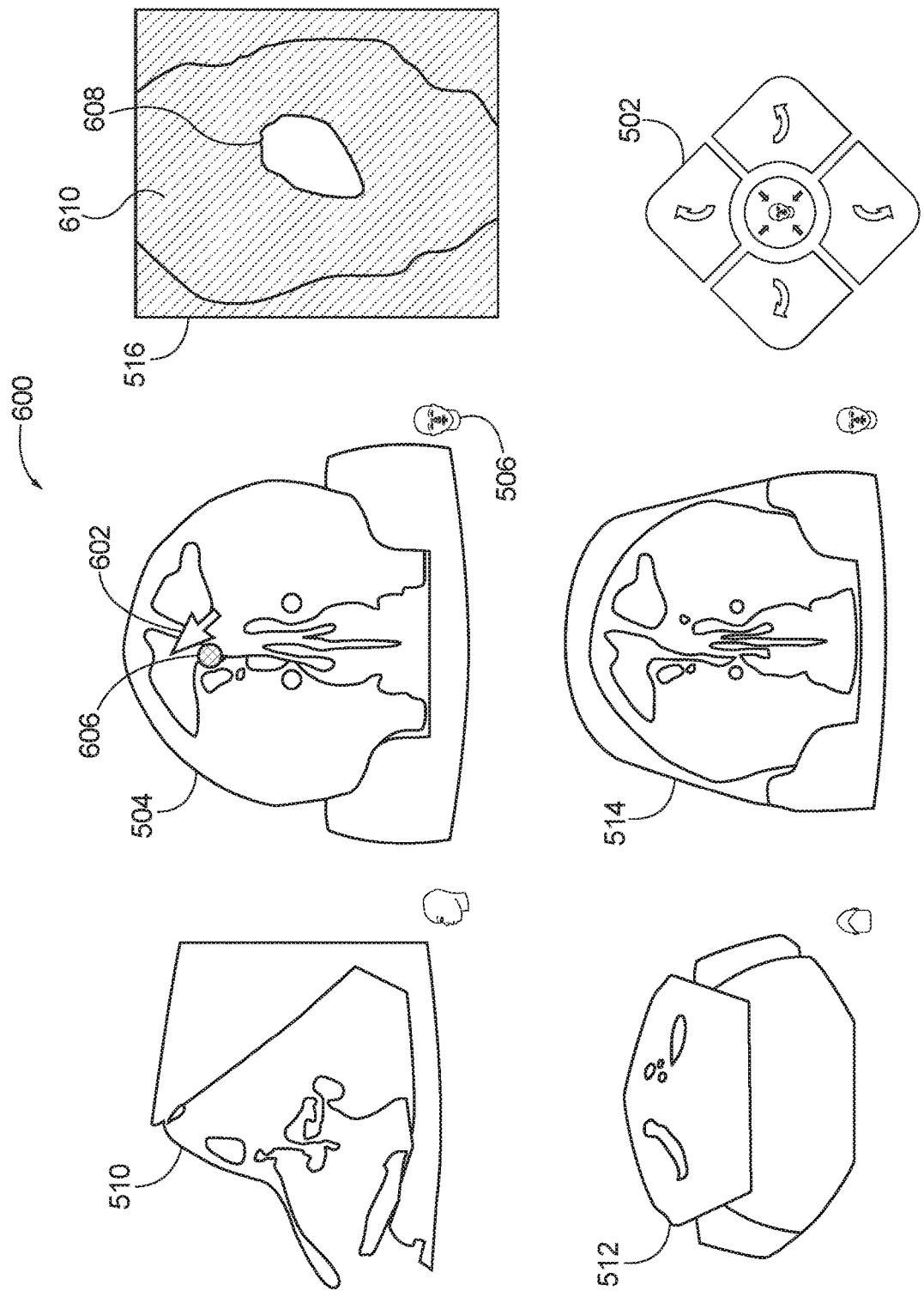
FIG. 12 shows a simulated screenshot of the alternate placement interface of FIG. 10 providing a third preview.

In FIG. 12, the cursor (602) has moved to a subsequent new position, along a y-axis of the frontal image (504) (e.g., the cursor (602) has moved vertically upwards while maintaining the same horizontal position). The portion (608) displayed in FIG. 11 is still visible but is now a subcomponent of a new portion (610) selected from the image slice based on the cursor's (602) new position relative to the marker (606). Since the cursor (602) has been moved vertically away from the marker (606) the portion (608) is now depicted with a smaller scale, while additional bone and tissue can now be seen in the portion (610).

Figure 13:
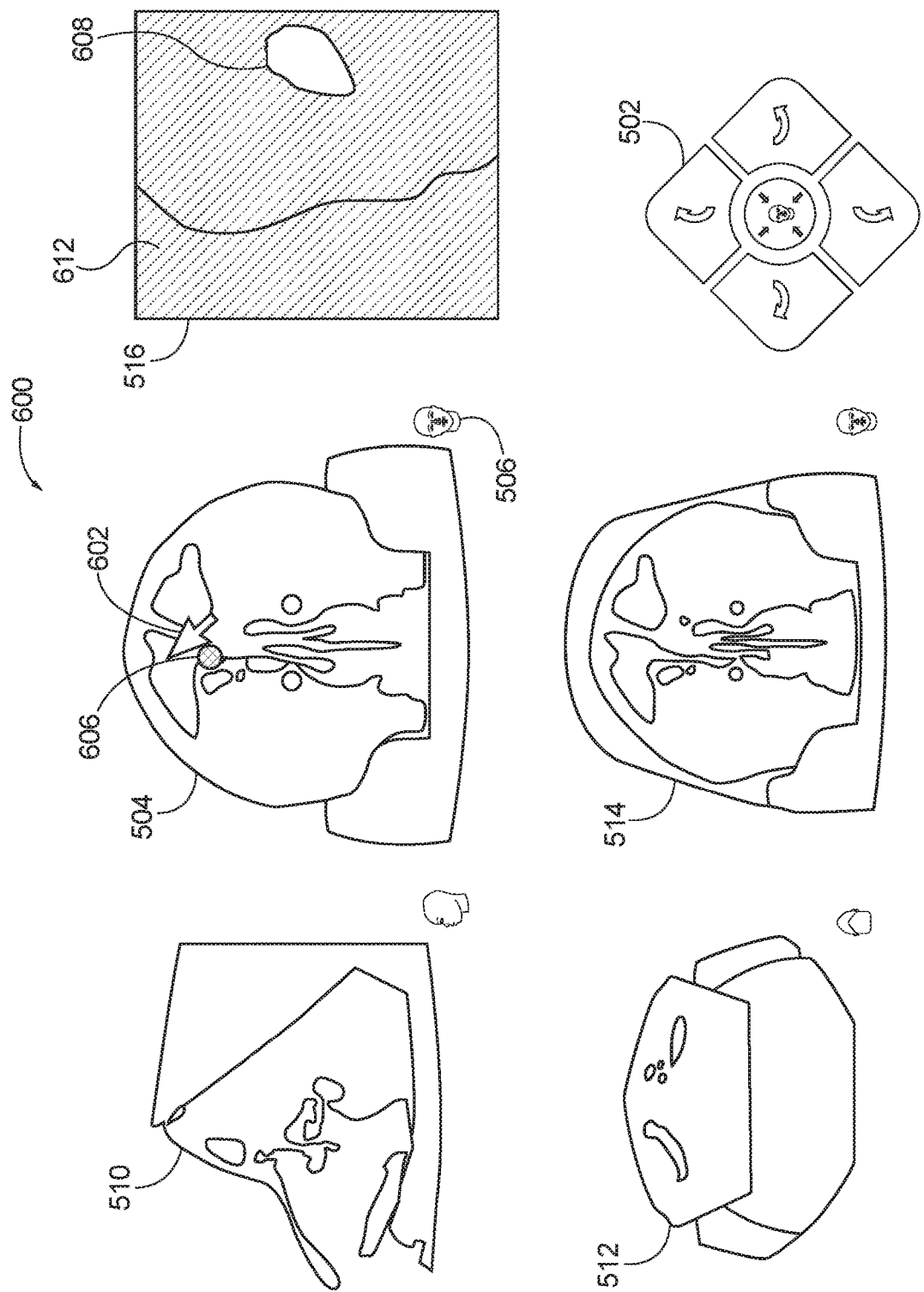
FIG. 13 shows a simulated screenshot of the alternate placement interface of FIG. 10 providing a fourth preview.

In FIG. 13, the cursor (602) has moved to a subsequent new position, along an x-axis of the frontal image (504) (e.g., horizontally while maintaining the same vertical position). The portion (608) is still largely visible, but as a subcomponent of a new portion (612) selected from the image slice based on the cursor's (602) new position relative to the marker (606). The scale of the portion (612) is unchanged, since the cursor (602) did not move vertically along the frontal image (504). As has been described, at any point during movement of the cursor (602) after defining (block 418) the first point a second point may be selected and defined by the system in order to finalize the virtual endoscope configuration. Fly-through viewing may be provided during configuration to aid in placement of the virtual endoscope by displaying fly-through viewing of one or more image slice. This may include displaying portions of a single image slice and changing their scale based upon movements of the cursor (602), may include stepping through image slices in sequence in order to provide a variable scale, or both.

In some implementations, the virtual camera view (516) may be configured to allow users to switch between viewing 3-D modeled anatomy and image slices, or may display both simultaneously. Whether the virtual camera view (516) displays 3-D modeled anatomy or image slices, the additional context provided by a fly-through viewing of the 3-D space surrounding the line between the first and second point may provide valuable visual context to a clinician configuring a virtual camera, as it may reveal that the virtual camera's potential position and orientation will result in a non-targeted anatomical structure blocking visibility of an important area of the surgical site, that the important area is not actually located between or around the line formed by the first and second point; or that the important area of the surgical site may be better viewed from a different first point, for example. If this is the case, the clinician may move the cursor (508) to a separate location in the preoperative image panes in order to cause the IGS navigation system (100) to determine (block 410) the new cursor (508) position and render (block 420) an updated relational preview based upon the new position, in real-time. While the descriptions of FIG. 3 describe rendering (block 414) a preview prior to a user selecting a first point and rendering (block 420) a relational preview prior to a user selecting a second point, it should understand that various implementations of the described interface and method may include one or both previews. For example, some implementations may only render (block 420) the relational preview, with the virtual camera view (block 416) being blank or showing arbitrary or other image data prior to the first point being defined (block 412).

Where the clinician is satisfied with the current placement of the virtual camera at the first point (509), and orientation of the virtual camera towards the current location of the cursor (508) based upon the flythrough preview of the interior anatomy view, the IGS navigation system (100) may receive (522) a second user selection and define (block 424) the second point based thereon. With the first point defined (block 412) and the second point defined (block 422), the virtual camera view (516) may continue to show the most recent rendered (block 420) relational preview or other images to allow the clinician to review (block 426) and confirm the virtual camera placement and orientation before finalizing and generating a virtual camera definition that may be used by the IGS navigation system (100) during a surgical procedure.

Figure 4:
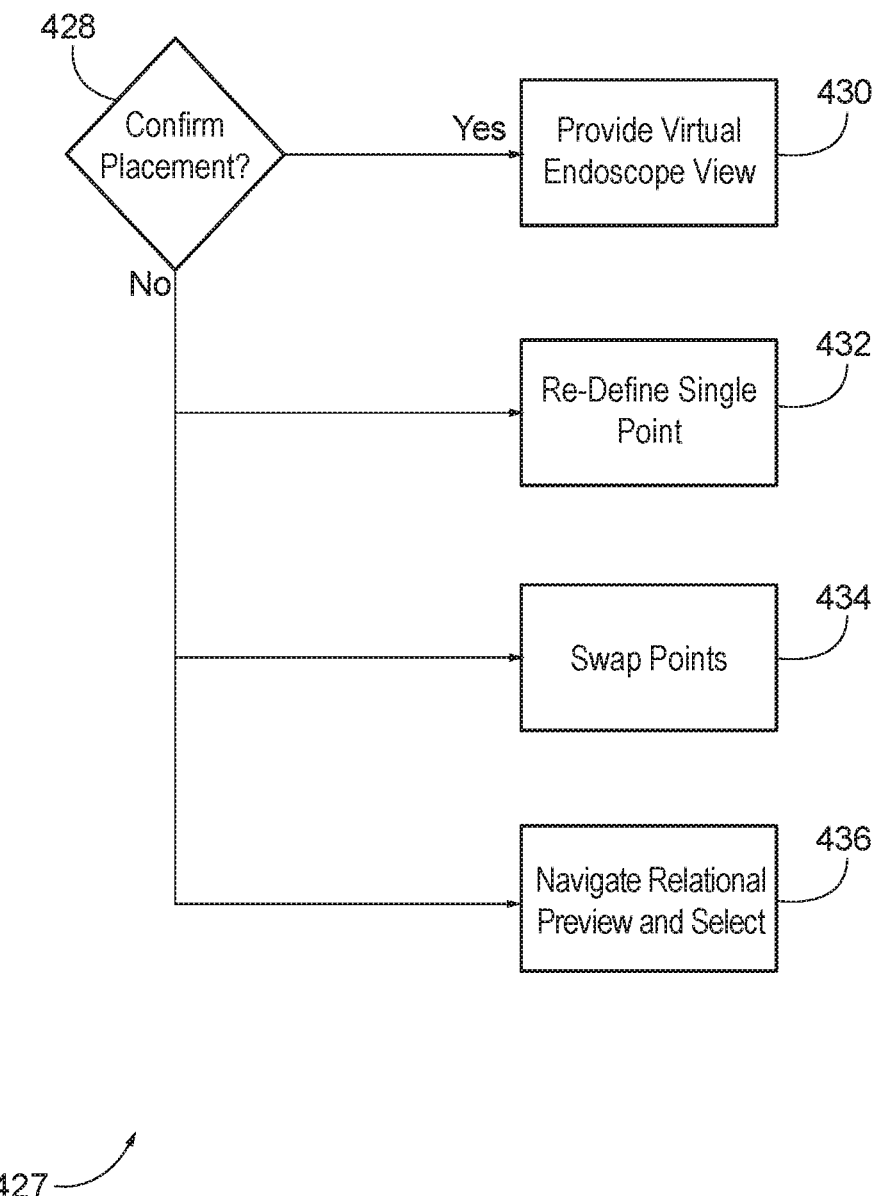
FIG. 4 shows an exemplary set of steps that may be performed by or with the surgery navigation system to review, modify, and confirm placement of a virtual camera.
Figure 5:
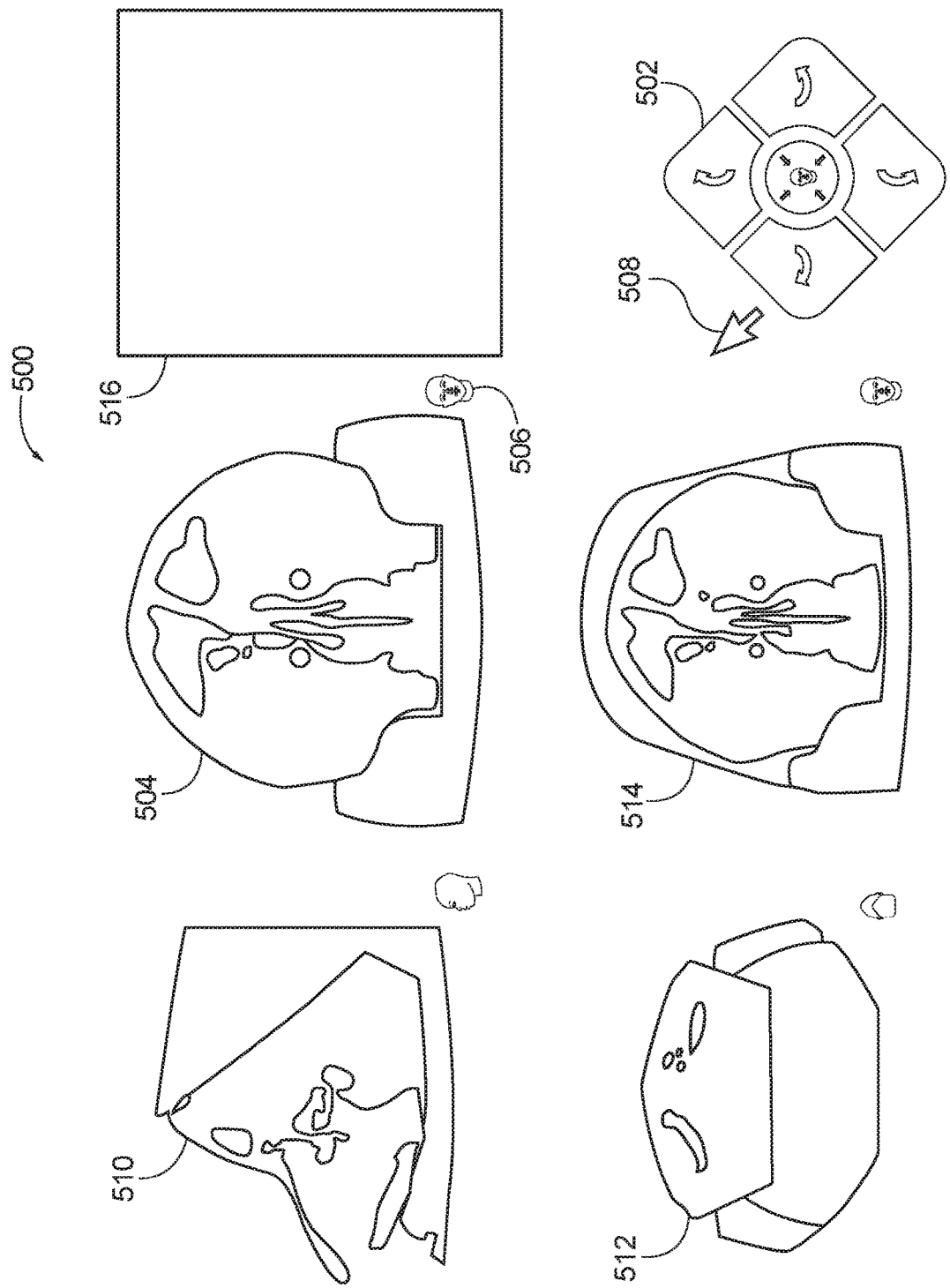
FIG. 5 shows a simulated screenshot of an exemplary placement interface.

FIG. 4 shows an exemplary set of steps (427) that may be performed by or with a surgery navigation system such as the IGS navigation system (100) to review, modify, and confirm placement of a virtual camera. Prior to confirming (block 428) the virtual camera placement and orientation, the cursor (508) or other user inputs may be used to interact with the set of navigation controls (502) or other use inputs to control the rendered (block 420) relational preview if the clinician wishes to, for example, control the speed of the flythrough or pause the flythrough at various points to aid in review. Based on user inputs, the areas surrounding the flythrough may be navigated (block 436) by repositioning the camera along the route, or by changing the orientation of the camera along the route. For example, a clinician might see something of concern in the flythrough, and may pause the preview, move the virtual camera off the flythrough route and through 3-D space to a separate point along one or more of the X, Y, and Z axis, and then rotate the orientation of the camera upwards to view something above and to the side of the flythrough route in more detail.

A user selection during such navigation (block 436) may cause one or more of the first point or the second point to be redefined to new locations. For example, a user selection of a location of the virtual camera view (516) may cause one or more of the first point and the second point to be redefined. As another example, one or more of the preoperative image panes may be updated in real-time during such navigation (block 436) to display particular preoperative images associated with the 3-D space in which the virtual camera view (516) is currently positioned or facing, such that a subsequent selection or cursor (508) navigation of the newly updated preoperative image pane may cause one or more of the first point and the second point to be redefined based thereon.

Other features that may be available to a user prior to confirming (block 428) placement and orientation of the virtual camera may include discarding and re-defining (block 432) the first point or the second point, and swapping (block 434) the first and second point. In some cases after viewing the relational flythrough, the clinician may determine that either of the selected points does not provide the desired virtual endoscopic view of the surgical site. In such a case, one or both defined points may be discarded, returning the clinician to the appropriate placement interface (500) state and step of FIG. 3.

Swapping (block 434) the first and second points (i.e., using the second point as the position of the virtual camera, and using the first point as the orientation of the virtual camera) may be activated by a clinician based upon one or more user inputs. It may be advantageous to provide such functionality with a single click, such that a clinician may view an initially rendered relational preview, swap (block 434) the points and view the preview in reverse to determine if it provides a more desirable view, and then swap (block 434) again to return to the original if it does not.

Improving the usability and simplicity of interfaces such as the placement interface (500) provides numerous advantages to users. The disclosed interfaces and methods can reduce placement of a virtual camera in 3-D operative image space to a small number of mouse clicks, keyboard presses, or other inputs. For example, in some scenarios, a clinician or other user may be able to place and orient a virtual camera with as few as two selection inputs (e.g., a first selection (block 416) or mouse click to define (block 418) the first point, a second selection (block 422) or mouse click to define (block 424) the second point) and one navigational input (e.g., positioning a cursor over a location on a preoperative image). The automated real-time flythrough preview removes the need for additional selection inputs (e.g., manually navigating along a similar route by clicking a mouse on buttons of the set of navigation controls (502) to place, review, and confirm virtual camera location and orientation). This may be advantageous in that it both reduces the time requires to configure the virtual camera, and in that it reduces both the number of and complexity of interactions (e.g., mouse, keyboard, or other input selections) that the clinician has with interface and the operating controls (112), which may be beneficial in maintaining a sterile environment in addition to other benefits.

After receiving confirmation (block 428) of the placement and orientation of the virtual camera, the IGS navigation system (100) may finalize placement by saving the first and second point and other associated data produced during the steps of FIGS. 2-4 into a virtual camera definition or other configuration set so that the virtual camera may be automatically repositioned in the future in order to provide (block 430) the desired virtual endoscopic view during an associated surgical procedure.

Variations on the systems, methods, and interfaces described above exist and will be apparent to one of ordinary skill in the art in light of this disclosure. For example, while some of the above discussion has described the first point as being the virtual camera's location, it should be understood that in some implementations the first point may be the virtual camera's orientation. This may be advantageous where a clinician has determined a position within the surgical area that is of interest and wishes to select that as the point of orientation (i.e., the second point), then preview a number of camera positions (e.g., the first point) using the real-time virtual endoscopic preview and relational flythrough before making a selection. Choosing the virtual camera's location as the first point may be advantageous where a clinician may use their experience to first determine the best location for the virtual camera, and then may use the real-time virtual endoscopic preview and relational flythrough to choose a point of the surgical area that they would like to focus the virtual camera upon.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system comprising: (a) a display; (b) a user input; (c) a set of preoperative images; and (d) a processor configured to provide a virtual camera placement interface to a user via the display and receive inputs via the user input the virtual camera placement interface comprising a set of preoperative image panes and a virtual camera view, wherein each of the set of preoperative image panes comprises a preoperative image from the set of preoperative images, and wherein the user input is operable to move a cursor over and make selections from the set of preoperative image panes, wherein the processor is further configured to: (i) define a first point based upon a first selection received via the user input, wherein the first selection comprises a point on one of the set of preoperative image panes, (ii) define a second point based upon a cursor position of the cursor on one of the set of preoperative image panes, and (iii) display a real-time virtual endoscopic preview in the virtual camera view based upon the first point and the second point.

Example 2

The system of Example 1, wherein the processor is further configured to: (i) change the value of the second point as the cursor moves and the cursor position changes, and (ii) update the real-time virtual endoscopic preview as the second point is changed.

Example 3

The system of any one or more of Examples 1 through 2, wherein the processor is further configured to: (i) after displaying the real-time virtual endoscopic preview, receive a second selection via the user input, wherein the second selection comprises a selected second point determined based upon the second point, and (ii) create a virtual camera definition based upon the first point and the selected second point, wherein the virtual camera definition is configured to be usable by an image guided surgery navigation system to produce a virtual endoscopic view during a surgical procedure.

Example 4

The system of Example 3, wherein the system comprises the image guided surgery navigation system, and wherein the user input comprises a pointing device.

Example 5

The system of any one or more of Examples 1 through 4, wherein the processor is further configured to, when displaying the real-time virtual endoscopic preview: (i) determine a spatial relationship between the first point and the second point, (ii) create a route through the set of preoperative images based upon the spatial relationship, and (iii) display a sequence of flythrough images in the virtual camera view based upon the route.

Example 6

The system of Example 5, wherein the sequence of flythrough images comprises a plurality of sequential images selected from the set of preoperative images and arranged in the order that they would be viewed while traversing the route.

Example 7

The system of any one or more Examples 5 through 6, wherein the virtual camera placement interface comprises a set of navigation controls, and wherein the processor is further configured to, in response to inputs via the set of navigation controls, adjust the speed and order at which the sequence of flythrough images is displayed.

Example 8

The system of Example 7, wherein the processor is further configured to, in response to inputs via the set of navigations controls: (i) pause the sequence of flythrough images, (ii) display a new image from the set of preoperative images in the virtual camera view based upon inputs indicating a change to one or both of the view position and orientation from an initial view position and orientation provided by the route, and (iii) change the value of one or both of the first point and the second point based upon the new image.

Example 9

The system of Example 8, wherein the processor is further configured to, when the new image is displayed, update one or more of the preoperative image panes to comprise a new preoperative image from the set of preoperative images, wherein the new preoperative image for each is determined based upon its proximity and relationship to the new image.

Example 10

The system of any one or more of Examples 5-9, wherein the first point is associated with a location of a virtual camera and the second point is associated with an orientation of the virtual camera, and wherein the route comprises a start point based that is determined based upon the first point and an end point that is determined based upon the second point.

Example 11

The system of any one or more of Examples 5-10, wherein the second point is associated with a location of a virtual camera and the first point is associated with an orientation of the virtual camera, and wherein the route comprises a start point based that is determined based upon the second point and an end point that is determined based upon the first point.

Example 12

The system of any one or more of Examples 1-11, wherein the processor is further configured to: (i) after displaying the real-time virtual endoscopic preview, receive a second selection via the user input, wherein the second selection comprises a selected second point determined based upon the second point, (ii) based upon a swap selection received via the user input, swap the values of the first point and the selected second point, and (iii) display the real-time virtual endoscopic preview in the virtual camera view based upon the changed values of the first point and the selected second point.

Example 13

The system of any one or more of Examples 1 through 12, wherein the processor is further configured to: (i) after displaying the real-time virtual endoscopic preview, receive a second selection via the user input, wherein the second selection comprises a selected second point determined based upon the second point, (ii) based upon a modify selection received via the user input, discard the selected value of one of the first point or the selected second point, (iii) define a modified point based upon the cursor position, wherein the modified point is the point whose value was discarded, and (iv) display the real-time virtual endoscopic preview in the virtual camera view based upon a retained point and the modified point, wherein the retained point is the point whose value was not discarded.

Example 14

The system of any one or more of Examples 1 through 14, wherein the processor is further configured to, prior to the first selection being received via the user input: (i) define the first point based upon the cursor position on one of the set of preoperative image panes, wherein that preoperative image pane is associated with a preoperative image of the set of preoperative images, and wherein the preoperative image comprises a perspective indicating an orientation from which the preoperative image is viewed, (ii) define the second point based upon the perspective of the preoperative image, and (iii) display the real-time virtual endoscopic preview in the virtual camera view based upon the first point and the second point.

Example 15

A method for configuring a virtual camera in 3-D space with a virtual camera placement interface, comprising the steps: (a) displaying a set of preoperative image panes via the virtual camera placement interface, wherein each of the set of preoperative image panes comprises a preoperative image from a set of preoperative images associated with a patient; (b) defining a first point based upon receiving a first selection from a user via the virtual camera placement interface, wherein the first selection comprises a point on one of the set of preoperative image panes; (c) defining a second point based upon a cursor position of a cursor on one of the set of preoperative image panes; (d) displaying a real-time virtual endoscopic preview via the virtual camera placement interface based upon the first point and the second point; and (e) changing the value of the second point as the cursor is moved by the user and the cursor position changes.

Example 16

The method of Example 15, further comprising the steps: (a) after displaying the real-time virtual endoscopic preview, receiving a second selection from the user via the virtual camera placement interface, wherein the second selection comprises a selected third point based upon the second point; and (b) creating a virtual camera definition based upon the first point and the selected third point, wherein the virtual camera definition is configured to be usable by an image guided surgery navigation system to produce a virtual endoscopic view during the surgical procedure.

Example 17

The method of Example 16, wherein the first selection is the only selection input received from the user prior to displaying the real-time virtual endoscopic preview; and wherein the second selection is the only selection input received from the user after receiving the first selection and prior to creating the virtual camera definition.

Example 18

The method of any one or more of Examples 15-17, further comprising the steps: (a) determining a spatial relationship between the first point and the second point, (b) creating a route through the set of preoperative images based upon the spatial relationship, and (c) displaying a sequence of flythrough images via the virtual camera placement interface based upon the route.

Example 19

The method of Example 18, wherein the sequence of flythrough images comprise a plurality of sequential images selected from the set of preoperative images and arranged in the order that they would be viewed while traversing the route.

Example 20

A system comprising: (a) a display; (b) a user input; (c) a set of preoperative images; and (d) a processor configured to provide a virtual camera placement interface to a user via the display and receive inputs via the user input, the virtual camera placement interface comprising a set of preoperative image panes and a virtual camera view, wherein each of the set of preoperative image panes comprises a preoperative image from the set of preoperative images, and wherein the user input is operable to move a cursor over and make selections from the set of preoperative image panes, wherein the processor is further configured to: (i) define a static point based upon a first selection received via the user input, wherein the first selection comprises a point on one of the set of preoperative image panes, (ii) define a dynamic point based upon a cursor position of the cursor on one of the set of preoperative image panes, (iii) display a real-time virtual endoscopic preview in the virtual camera view based upon the static point and the dynamic point, (iv) after displaying the real-time virtual endoscopic preview, receive a second selection via the user input and define a second static point based upon the second selection, wherein the second selection comprises the dynamic point, and (v) create a virtual camera definition based upon the static point and the second static point, wherein the virtual camera definition is configured to be usable by an image guided surgery navigation system to produce a virtual endoscopic view during a surgical procedure.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
   (a) a display;
   (b) user input;
   (c) a set of preoperative images associated with a patient; and
   (d) a processor configured to provide a virtual camera placement interface to a user via the display and receive inputs via the user input;
   wherein the virtual camera placement interface comprises a set of preoperative image panes and a virtual camera view, wherein each of the set of preoperative image panes corresponds to a viewpoint, wherein the set of preoperative image panes comprises preoperative image panes corresponding to a top-down viewpoint, a side viewpoint, and a frontal viewpoint, wherein each of the set of preoperative image panes comprises a preoperative image from the set of preoperative images displayed from the viewpoint corresponding to the preoperative image pane which comprises it, and wherein the user input is operable to move a cursor over and make selections from the set of preoperative image panes,
   wherein the processor is further configured to:
      (i) define a first point based upon a first selection received via the user input, wherein the first selection comprises a point on one of the set of preoperative image panes that corresponds to a first cursor position of the cursor when the first selection is received and is based upon the viewpoint corresponding to the preoperative image pane comprising the point corresponding to the first cursor position of the cursor when the first selection is received,
      (ii) define a second point based upon (A) a second cursor position of the cursor located on any of the set of preoperative image panes, and (B) the viewpoint corresponding to the preoperative image pane on which the second cursor position is located, and
      (iii) display a real-time virtual endoscopic preview in the virtual camera view based upon the first point and the second point.

2. The system of claim 1, wherein the processor is further configured to:
   (i) change the value of the second point as the cursor moves and the second cursor position changes, and
   (ii) update the real-time virtual endoscopic preview as the second point is changed.

3. The system of claim 1, wherein the processor is further configured to:
   (i) after displaying the real-time virtual endoscopic preview, receive a second selection via the user input, wherein the second selection comprises a selected second point determined based upon the second point, and
   (ii) create a virtual camera definition based upon the first point and the selected second point, wherein the virtual camera definition is configured to be usable by an image guided surgery navigation system to produce a virtual endoscopic view during a surgical procedure.

4. The system of claim 3, wherein the system comprises the image guided surgery navigation system, and wherein the user input comprises a pointing device.

5. The system of claim 1, wherein the processor is further configured to, when displaying the real-time virtual endoscopic preview:
   (i) determine a spatial relationship between the first point and the second point,
   (ii) create a route through the set of preoperative images based upon the spatial relationship, and
   (iii) display a sequence of flythrough images in the virtual camera view based upon the route.

6. The system of claim 5, wherein the sequence of flythrough images comprises a plurality of sequential images selected from the set of preoperative images and arranged in the order that they would be viewed while traversing the route.

7. The system of claim 5, wherein the virtual camera placement interface comprises a set of navigation controls, and wherein the processor is further configured to, in response to inputs via the set of navigation controls, adjust the speed and order at which the sequence of flythrough images is displayed.

8. The system of claim 7, wherein the processor is further configured to, in response to inputs via the set of navigations controls:
   (i) pause display of the sequence of flythrough images,
   (ii) display a new image from the set of preoperative images in the virtual camera view based upon inputs indicating a change to one or both of the view position and orientation from an initial view position and orientation provided by the route, and
   (iii) change the value of one or both of the first point and the second point based upon the new image.

9. The system of claim 8, wherein the processor is further configured to, when the new image is displayed, update one or more of the preoperative image panes to comprise a new preoperative image from the set of preoperative images, wherein the new preoperative image for each is determined based upon its proximity and relationship to the new image.

10. The system of claim 5, wherein the first point is associated with a location of a virtual camera and the second point is associated with an orientation of the virtual camera, and wherein the route comprises a start point that is determined based upon the first point and an end point that is determined based upon the second point.

11. The system of claim 5, wherein the second point is associated with a location of a virtual camera and the first point is associated with an orientation of the virtual camera, and wherein the route comprises a start point that is determined based upon the second point and an end point that is determined based upon the first point.

12. The system of claim 1, wherein the processor is further configured to:
   (i) after displaying the real-time virtual endoscopic preview, receive a second selection via the user input, wherein the second selection comprises a selected second point determined based upon the second point,
   (ii) display the real-time virtual endoscopic preview in the virtual camera view based on a virtual camera located at the first point and oriented toward the selected second point,
   (iii) based upon a swap selection received via the user input, swap the values of the first point and the selected second point, and
   (iv) display the real-time virtual endoscopic preview in the virtual camera view based upon a virtual camera located at the changed first point and oriented toward the changed selected second point.

13. The system of claim 1, wherein the processor is further configured to:
(i) after displaying the real-time virtual endoscopic preview, receive a second selection via the user input, wherein the second selection comprises a selected second point determined based upon the second point,
(ii) based upon a modify selection received via the user input, discard the selected value of one of the first point or the selected second point,
(iii) define a modified point based upon a third cursor position, wherein the modified point is the point whose value was discarded, and
(iv) display the real-time virtual endoscopic preview in the virtual camera view based upon a retained point and the modified point, wherein the retained point is the point whose value was not discarded.

14. The system of claim 1, wherein the processor is further configured to, prior to the first selection being received via the user input:
(i) define the first point based upon the first cursor position located on one of the set of preoperative image panes,
(ii) define the second point based upon the viewpoint corresponding to the preoperative image pane on which the first cursor position is located, and
(iii) display the real-time virtual endoscopic preview in the virtual camera view based upon the first point and the second point.

15. A method for configuring a virtual camera in 3-D space with a virtual camera placement interface, comprising the steps:
(a) displaying a set of preoperative image panes via the virtual camera placement interface, wherein each of the set of preoperative image panes corresponds to a viewpoint, wherein the set of preoperative image panes comprises preoperative image panes corresponding to a top-down viewpoint, a side viewpoint, and a frontal viewpoint, wherein each of the set of preoperative image panes comprises a preoperative image from a set of preoperative images associated with a patient displayed from the viewpoint corresponding to the preoperative image pane which comprises it;
(b) defining a first point based upon receiving a first selection from a user via the virtual camera placement interface, wherein the first selection comprises a point on one of the set of preoperative image panes that corresponds to a first cursor position of a cursor positioned by the user over that preoperative image pane and is based upon the viewpoint corresponding to that preoperative image pane;
(c) defining a second point based upon (i) a second cursor position of the cursor located on any of the set of preoperative image panes, and (ii) the viewpoint corresponding to the preoperative image pane on which the second cursor position is located;
(d) displaying a real-time virtual endoscopic preview via the virtual camera placement interface based upon the first point and the second point; and
(e) changing the value of the second point as the cursor is moved by the user and the second cursor position changes.

16. The method of claim 15, further comprising the steps:
(a) after displaying the real-time virtual endoscopic preview, receiving a second selection from the user via the virtual camera placement interface, wherein the second selection comprises a selected third point based upon the second point; and
(b) creating a virtual camera definition based upon the first point and the selected third point, wherein the virtual camera definition is configured to be usable by an image guided surgery navigation system to produce a virtual endoscopic view during a surgical procedure.

17. The method of claim 16, wherein the first selection is the only selection input received from the user prior to displaying the real-time virtual endoscopic preview; and
wherein the second selection is the only selection input received from the user after receiving the first selection and prior to creating the virtual camera definition.

18. The method of claim 15, further comprising the steps:
(a) determining a spatial relationship between the first point and the second point;
(b) creating a route through the set of preoperative images based upon the spatial relationship; and
(c) displaying a sequence of flythrough images via the virtual camera placement interface based upon the route.

19. The method of claim 18, wherein the sequence of flythrough images comprise a plurality of sequential images selected from the set of preoperative images and arranged in the order that they would be viewed while traversing the route.

20. A system comprising:
(a) a display;
(b) user input;
(c) a set of preoperative images associated with a patient; and
(d) a processor configured to provide a virtual camera placement interface to a user via the display and receive inputs via the user input; the virtual camera placement interface comprising a set of preoperative image panes and a virtual camera view, wherein each of the set of preoperative image panes comprises a preoperative image from the set of preoperative images, and wherein the user input is operable to move a cursor over and make selections from the set of preoperative image panes,
wherein the processor is further configured to:
(i) define a first point based upon a first selection received via the user input, wherein the first selection comprises a point on one of the set of preoperative image panes,
(ii) define a second point based upon a cursor position of the cursor on one of the set of preoperative image panes,
(iii) display a real-time virtual endoscopic preview in the virtual camera view based upon the first point and the second point,
(iv) receive a second selection via the user input, wherein the second selection comprises a selected second point determined based upon the second point,
(v) based upon a modify selection received via the user input, discard the selected value of one of the first point or the selected second point,
(vi) define a modified point based upon the cursor position, wherein the modified point is the point whose value was discarded, and
(vii) display the real-time virtual endoscopic preview in the virtual camera view based upon a retained point and the modified point, wherein the retained point is the point whose value was not discarded.

* * * * *